(12) United States Patent
Fischer et al.

(10) Patent No.: US 7,357,504 B2
(45) Date of Patent: Apr. 15, 2008

(54) DEVICE AND METHOD FOR EXAMINING AND/OR TREATING AND EYE

(75) Inventors: Konrad Fischer, Bern (CH); Juan Manu Teijido, Auvernier (CH)

(73) Assignee: Haag-Streit AG, Koniz (CH)

( * ) Notice: Subject to any disclaimer, the term of this patent is extended or adjusted under 35 U.S.C. 154(b) by 381 days.

(21) Appl. No.: 10/416,854

(22) PCT Filed: Nov. 15, 2001

(86) PCT No.: PCT/CH01/00669

§ 371 (c)(1),
(2), (4) Date: Sep. 3, 2003

(87) PCT Pub. No.: WO02/39892

PCT Pub. Date: May 23, 2002

(65) Prior Publication Data

US 2004/0036839 A1    Feb. 26, 2004

(30) Foreign Application Priority Data

Nov. 17, 2000   (EP) .................................. 00811094

(51) Int. Cl.
*A61B 3/00*    (2006.01)

(52) U.S. Cl. ........................ 351/200; 351/219
(58) Field of Classification Search ................ 351/204, 351/217, 234, 219, 200, 205, 212, 213, 247; 128/645

See application file for complete search history.

(56) References Cited

U.S. PATENT DOCUMENTS

| 4,065,208 | A | * | 12/1977 | Currey ........................ 351/219 |
| 4,270,842 | A |   | 6/1981  | Muchel et al. |
| 4,367,018 | A | * | 1/1983  | Abe ............................ 351/213 |
| 5,022,749 | A |   | 6/1991  | Ogura et al. |
| 5,031,622 | A |   | 7/1991  | LaHaye |
| 5,347,326 | A | * | 9/1994  | Volk ........................ 351/160 R |
| 5,479,222 | A | * | 12/1995 | Volk ............................ 351/219 |
| 5,501,217 | A |   | 3/1996  | Ishiguro et al. |
| 5,841,510 | A |   | 11/1998 | Roggy |
| 6,183,085 | B1 | * | 2/2001  | Roggy et al. ............... 351/200 |
| 6,698,886 | B2 | * | 3/2004  | Pollack et al. ............. 351/219 |
| 6,976,758 | B2 | * | 12/2005 | Khaw et al. ................ 351/219 |

FOREIGN PATENT DOCUMENTS

| DE | 30 32 164 A    | 4/1981 |
| JP | S51-102291     | 9/1976 |
| JP | S63-070630     | 3/1988 |
| WO | WO 00 57773 A  | 10/2000 |

* cited by examiner

*Primary Examiner*—Huy K Mai
(74) *Attorney, Agent, or Firm*—Birch, Stewart, Kolasch & Birch, LLP

(57) ABSTRACT

A device for examining/treating an eye has a base body and an attachment body, which can be combined and applied to the eye. A gel-type liquid is introduced between the two bodies so that the indices can be matched. The interior of the attachment body is provided with a large number of protuberances, ensuring a minimum distance is maintained between the two bodies, allowing air or excess liquid to escape between the two bodies to escape. Only the attachment body, a disposable item producible from cheap materials, needs to be sterilized and a single sterilization is integrated into the production process. The base only needs to be disinfected. This division of the device also allows a large number of base bodies with different configurations to be used with one single attachment body or a large number of attachment bodies with different configurations to be used with one single base body.

15 Claims, 2 Drawing Sheets

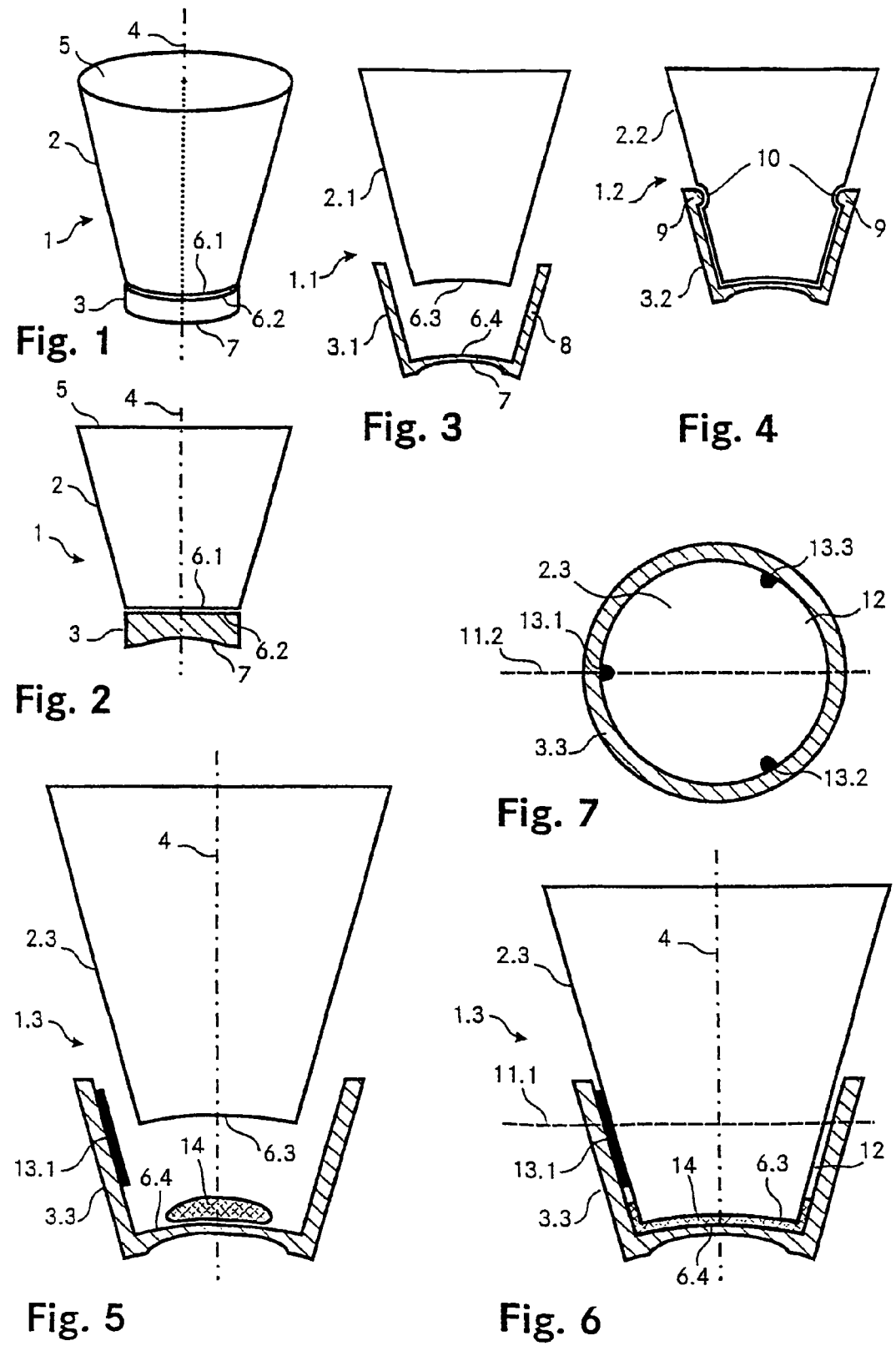

DEVICE AND METHOD FOR EXAMINING AND/OR TREATING AND EYE

This application is the national phase under 35 U.S.C. 371 of PCT International Application No. PCT/CH01/00669 which has an International filing date of Nov. 15, 2001, which designated the United States of America.

TECHNICAL FIELD

The invention relates to a device for examining and/or treating an eye, it being intended to be placed on the eye.

PRIOR ART

The prior art discloses various devices for examining and/or treating eyes that are placed directly on the eye in order to examine and/or treat the latter. For the sake of simplicity, the term examination is to be understood below as an appropriate treatment of the eye as well, in each case.

Such devices for examining eyes include, for example, so-called contact glasses which permit examination or treatment of the fundus of the eye or other regions in the interior of the eye through the pupil of the eye. However, this may also include other devices such as, for example, tonometers, which can be brought directly into contact with the eye for the purpose of eye pressure measurement.

Such devices are produced and marketed in many different variants. For example, there are various sizes for contact glasses for adults or children. Depending on the application desired, they can also have one or more, laterally arranged mirrors with the aid of which peripheral regions of the interior of the eye can be examined which would not be visible without mirrors. Furthermore, there are also contact glasses which, in that region which is brought into contact with the eye, have a so-called scleral ring that rests on the eye in the examination position in such a way that it is covered by the eyelids and held by the latter on the eye.

The known devices have the disadvantage that, firstly, different embodiments of the device need to be held ready for various examinations. Also, in order to prevent the eye being contaminated during the examination and thus also increasing the risk of infections, the devices must, secondly, be disinfected and/or sterilized before each use. However, this is wear phenomena, for which reason the devices must be replaced from time to time.

SUMMARY OF THE INVENTION

It is an object of the invention to specify a device of the type mentioned that avoids the disadvantages of the devices known from the prior art and prevent a transmission of infections or irritating elements in a simple way. A cost effective and simple possibility for examining eyes should in particular also be provided.

The achievement of the object is defined by the features of claim 1. In accordance with the invention, the device for examining and/or treating an eye, which is intended to be placed on the eye, has a base body and an attachment body that can be combined with the base body, the device for examining and/or treating the eye being intended to be placed with the attachment body on the eye.

This division of the device into a base body and an attachment body has many advantages. Thus, the base body can optionally be provided with, for example, particular optical elements for examining eyes such as one or more mirrors, or with specific lens arrangements. A large part of the mechanical and/or optical complexity therefore resides in the base body.

The attachment body therefore requires no optically active elements, but typically consists only of a thin layer of optically transparent material. It can be produced in large quantities in a simple and cost effective way. It can, on the one hand, be designed as a disposable article to be used once or a few times. On the other hand, it can be designed for repeated use, also being capable of replacement by a new one in a cost effective way if, for example, wear has become too great as a consequence of disinfection or sterilization. However, it is to be ensured that in that region which comes into contact with the eye the attachment body is designed such that the eye is not injured. Thus, for example, that surface of the attachment with which it is placed on the eye should not have any ridges or edges, but rather be of smooth design and be adapted to the surface of the eye.

It is possible furthermore, for example, for different attachment bodies to be attached to one and the same base body. This renders various examinations possible in a cost effective way, something for which the prior art requires various devices, which are expensive in each case.

Of course, it is also possible conversely to use a single attachment body or a single type of attachment body together with various base bodies, it thereby being possible to cover further variant devices.

By combining a few variants of attachment bodies with a few variants of base bodies, it is possible in practice to combine all variant devices, and this permits a multifarious and yet simple and cost effective examination of eyes.

The external form of the base body can be arbitrary in principle. However, it typically has a plane surface on one side, through which the eye can be examined. Furthermore, the base body preferably has a contact surface that is typically located opposite the plane surface. This contact surface can be both plane and optionally convex or concave, or be of arbitrary shape within specific limits.

The attachment body is preferably provided with a further contact surface, which is designed with substantially the same shape as the contact surface of the base body, the two contact surfaces being situated substantially parallel to one another when the device is combined. Of the same shape means, in essence, that the contact surfaces are not identical, but are designed in such a way that they have approximately the same shape and approximately the same size so that they can be brought into contact with one another. The two contact surfaces are designed, for example, in a plane fashion in the shape of a polygon with approximately the same side ratios and areas, or they are both round and have approximately the same diameter. If, by contrast, the contact surface of the base body has a camber inward or outward, the contact surface of the attachment body is provided with a corresponding camber outward or inward, respectively.

Parallel means, in essence, that plane contact surfaces come to be situated in parallel planes, and that in the case of cambered contact surfaces the camber of the attachment body corresponds approximately to the inverse camber of the base body so that they can be set one inside another, as it were. However, the radii of curvature of the cambers can certainly be slightly different such that the contact surfaces touch one another only at individual points. Interspaces, possibly filled with air, result in this way between the contact surfaces.

However, such interspaces have a disturbing effect during examination of the eye, since at such interfaces from a solid body to air and vice versa light beams are subjected to strong optical interference such as diffraction, reflection and scattering. In order to avoid or to reduce such interference, an optically transparent, deformable intermediate material is now preferably introduced during combination of the device between the base body and the attachment body. This material is, for example, of gel-type or flowable design. It is also possible only to use elastically or plastically deformable material. The material is merely to be deformable in such a way that upon combination it lies snugly against the contact surfaces, the contact surfaces being shaped in such a way that upon combination no air bubbles, and/or only a few or small ones are enclosed. Use is made for the intermediate material of a material whose refractive index corresponds approximately to the refractive index of base body and attachment body. The more precisely the refractive indices of base body, attachment body and deformable material correspond, the lesser is the resulting interference. It is possible thereby for the contact surfaces to be produced with a low optical quality, and thus cost effectively. Expensive grinding and/or other coating operations such as, for example, antireflection coating, as are required in the production of optical surfaces of high quality, are eliminated.

Introducing this deformable material between the base body and attachment body has yet a further advantage: owing to the adhesion-induced adhesive forces between the deformable material and base body, on the one hand, and the deformable material and the attachment body, on the other hand, the base body and the attachment body remain stuck to one another without the action of other, external forces. That is to say, depending on the design of the two bodies, for example given an attachment body of low weight, it is not necessary to provide additional connecting means between base body and attachment body. For the purpose of examining the eye by a user who grips the base body of the combined device in order to position the latter on the eye, the adhesive forces produced by the adhesion of the deformable material with the contact surfaces of base body and attachment body suffice to hold the attachment body on the base body.

In order, for example, to examine the chamber angle or other peripheral regions of the fundus of the eye using known devices, use is made, for example, of a contact glass that is not of symmetrical construction but has a mirror on one side. By looking into such a contact glass placed on an eye, it is possible to examine the chamber angle via the mirror fitted laterally at the correct angle. In order to be able to examine the peripheral region of the eye completely, the contact glass must be rotated, not being removed from the eye of the patient in the process. In known devices of the prior art, there is an increased risk of injury in this case. For example, the cornea of the eye can be damaged, or an eyelash trapped between cornea and contact glass can be torn out. Such irritation is, furthermore, extremely unpleasant for the patient.

In a preferred embodiment of the device according to the invention, the base body and the attachment body are designed in such a way that they can be rotated relative to one another in the combined state. This is to say, if the aim is to examine peripheral regions of an eye completely, it is possible in a way similar to the contact glass of the prior art to use a base body with an appropriate mirror. The latter is combined with a suitable attachment body to form the device, and the device is placed with the attachment body on the eye to be examined. By now rotating the base body relative to the attachment body, in particular about the optical axis of the two bodies, it is possible to examine the peripheral regions completely without corotating the attachment body in the process. The attachment body, which is the only part of the device to make contact with the eye, is thereby not moved.

In a possible embodiment of the device, both the base body and the attachment body are designed in a rotationally symmetrical fashion. The base body has, for example, the shape of a cone with apex cut off, and the attachment body has the shape of a funnel with a flattened base, the contact surface of the base body being located outside in the region of the flattened apex, and the contact surface of the attachment body being located on the inside of the flattened funnel base. The dimensions of the base body and attachment body are selected in this case in such a way that the base body can be inserted into the funnel and the contact between the contact surfaces can be produced in this way.

So that a certain minimum spacing is preserved between the base body and the attachment body outside the contact surfaces, that is to say, for example, in the region of the outer walls of the base body and the side walls of the funnel, either the base body itself or the attachment body has distancing elements, for example a plurality of protuberances, outside the respective contact surface. These can be designed, for example, in the shape of a plurality of knobs, in the form of webs, running in an elongated fashion, of the type of a comb, or in the form of two-dimensional protuberances.

A further, preferred embodiment of the invention is designed in such a way that when it is combined and placed on the patient's eye to be examined, the patient comes into contact only with the attachment body. That is to say, the eye itself, as well as the patient's eyelids or eyelashes, do not come into contact with the base body, assuming appropriate manipulation.

Since it does not come into direct contact with the eye or the patient, the base body need only be disinfected after use, but not sterilized. For this reason, it can be produced from materials such as, for example, plastic that are not only more cost effective, but which are also correspondingly easier to process than glass, for example.

In the case of the abovementioned funnel-shaped design of the attachment body, the funnel edge is, for example, so wide that the base body can be excluded from touching the eye and/or an eyelid or the eyelashes.

As already mentioned, the base body and attachment body can be designed in such a way that they adhere to one another after combination since, for example, their surfaces are designed in such a way, or the deformable material is located between the surfaces in such a way, that the adhesion forces suffice to hold them together. In a further, preferred embodiment of the device according to the invention for examining eyes, the base body and attachment body are designed in such a way that they are held together by a detachable, positive and/or non-positive connection. It is possible to conceive, for example, a screw connection, a type of toggle closure, a latching mechanism for producing a click-type connection, or another, arbitrary type of connection.

The use of a disconnectable connection between the base body and attachment body ensures that the attachment body can be removed from the base body after use, that is to say after the examination of an eye. It can, for example, be discarded thereafter, or is made from a material that permits sterilization of the attachment body, for example with the aid of an autoclave.

As already mentioned, the base body is designed in such a way that it permits an ophthalmological, in particular an optical examination of the eye. For example, it is produced from an optically transparent material through which light beams can pass both into the eye and out of the eye. In order to keep extraneous light away or to reduce interfering reflections at the lateral boundary surfaces, the latter can, for example, be colored dark or be coated with an appropriate material.

In order to examine the lateral regions of the fundus of the eye or of the chamber angle, the base body preferably has one or a plurality of mirrors. The mirrors are placed in this case in such a way that the view to the central fundus of the eye remains open. Each mirror further has a specific angle of inclination that permits a very specific region of the interior of the eye to be examined. Where there are a plurality of mirrors, the mirrors usually all have a different angle of inclination.

The base and attachment bodies described can, of course, also be designed in such a way that they can be used not only to examine but also to treat an eye, for example with the aid of a laser beam.

As likewise already mentioned, the device for examining the eye is placed with the attachment body on the eye in each case. Consequently, the attachment body preferably has a touch surface that is substantially adapted to a surface region of the eye to be examined. That is to say, the touch surface has a camber that corresponds approximately to the camber of the cornea of the eye to be examined. The touch surface is mostly situated on [lacuna] side of the attachment body opposite the contact surface.

In order to examine eyes of different size, as a consequence, different cambers, for example children's eyes by contrast with adult's eyes, differently cambered attachment bodies can be used with the same base body.

The shape of the touch surface can virtually be freely selected, a round shape being preferred. The size of the touch surface can also be freely selected within certain limits. The lower limit for the size is determined, on the one hand, by the quantity of light that is required for the examination and should, on the other hand, also not be selected so small that there is a risk of injury to the eye. In the case of round touch surfaces, the diameter should, for example, also not be selected larger than the greatest diameter of the visible part of the eye with eyelids open. The touch surface of typical attachment bodies corresponds approximately to the size of the iris.

However, there are individuals who, for example, tend to be rather unsettled, or in whom the spacing of the eyelids with opened eye is less than in the case of others. It is difficult with such individuals to hold the device placed on the eye in the correct position without fixing the eyelids with the aid of appropriate clamps, for example. In order to avoid this procedure, which is unpleasant for the patient, use is made of attachment bodies whose touch surface is preferably designed in such a way that it has edge regions that, when placed on the eye, can be pushed at least partially under at least one eyelid of the patient, and the attachment body is held in this way in the correct position by the eyelid or eyelids. Around the transparent region to be examined, for example, the touch surface has a type of ring, a so-called scleral ring, which is pushed under the eyelids when the attachment body is placed on the eye.

In order to ensure the device is manipulated correctly and as simply as possible, after production the attachment bodies are accommodated, preferably ready for use, in a container for storing or for transportation. Before this, the attachment bodies are typically sterilized and individually packed. Suitable for this purpose, for example, are so-called Blista packages, in the case of which the individual items are each located in a dedicated chamber of a container are covered by a film, in each case.

The container is, for example, designed in such a way that it permits the attachment body to be attached to the base body without the attachment body being touched by the user. The user firstly removes the film from the chamber with the desired attachment body, the sterile attachment body being situated in a special holder. The latter permits the user to apply the deformable material for example a gel-type liquid onto the contact surface and subsequently to attach the base body to be used to the attachment body, or to insert it into the latter, and to combine the device in this way.

Further advantageous embodiments and combinations of features of the invention emerge from the following detailed description and the totality of the patent claims.

BRIEF DESCRIPTION OF THE DRAWINGS

In the drawings used to explain the exemplary embodiment:

FIG. 1 shows a combined contact glass according to the invention for examining eyes, in a schematic, perspective representation;

FIG. 2 shows a sectional view of the contact glass from FIG. 1;

FIG. 3 shows a non-combined, other variant of the contact glass according to the invention;

FIG. 4 shows a combined, further variant of the contact glass with click-type connection between the base body and attachment body;

FIG. 5 shows a contact glass with an applied, gel-type material for adapting the refractive index, before the combination;

FIG. 6 shows the contact glass from FIG. 5 after the combination;

FIG. 7 shows a sectional view of the contact glass from FIG. 6;

Identical parts are provided in principle in the figures with identical reference numerals.

Ways of Implementing the Invention

Figure 8:
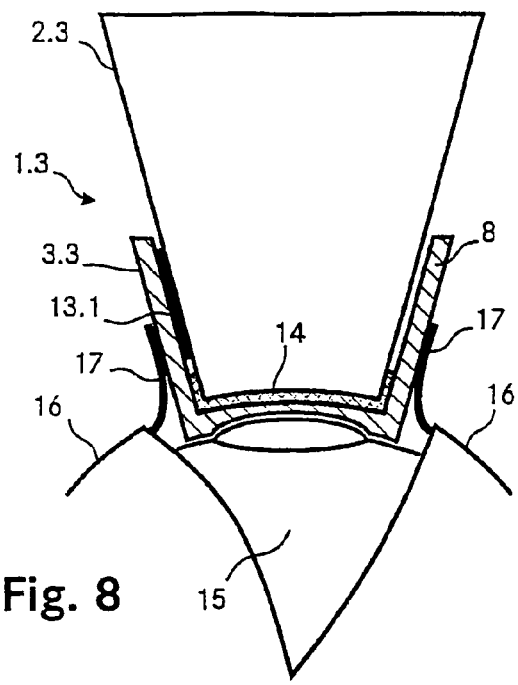
FIG. 8 shows the contact glass from FIG. 6 placed on an eye.

A few preferred variants of the invention are to be explained in more detail with the aid of the figures.

FIG. 1 shows a perspective, schematic representation of a contact glass 1 according to the invention for examining the interior of an eye. It comprises a base body 2 and an attachment body 3 that are illustrated in a combined fashion. The contact glass 1 is designed to be rotationally symmetrical relative to the rotation axis 4. A longitudinal section through the contact glass 1 is illustrated in FIG. 2, the plane of section containing the rotation axis 4 and dividing the contact glass 1 into two identical halves.

The base body 2 combined with the attachment body 3 forms a contact glass 1 in this case. When combined, it could just as well also form a tonometer measuring member that is placed on the eye under a specific pressure. The intraocular pressure can subsequently be determined from the measurable deformation of the surface of the eye and the pressure. Where this is sensible, the following description of the figures is also accordingly to be understood as a description of devices for measuring the intraocular pressure, in the case of which devices the base body is to be interpreted as a tonometer measuring member.

On its top side, the base body 2 has a plane, in this case circular, surface 5 preferably running perpendicular to the rotation axis 4. The likewise circular contact surface 6.1 of the base body 2 is located opposite the plane surface 5. On its top side, the attachment body 3 likewise has a once again circular contact surface 6.2, and on its underside it has a likewise circular touch surface 7. Both the base body 2 and the attachment body 3 are produced from an optically transparent material such as, for example, glass or from appropriate plastics such as, for example, Plexiglass, such that they are transparent to light and permit viewing through the body.

So that it is possible for the contact glass to be used even without a means to be introduced between the contact surfaces 6.1, 6.2 for index matching, that is to say adapting the refractive indices of the various materials, the contact surfaces 6.1, 6.2 are ground with a high optical quality, polished and/or given an antireflection coating. It would be possible thereby not only to reduce disturbing reflections at the contact surfaces 6.1, 6.2, but also to achieve a certain adhesion, caused by adhesion between the contact surfaces 6.1, 62, of the attachment body 3 on the base body 2, or vice versa.

In order to examine an eye, the contact glass 1 is placed by a user with the touch surface 7 on the eye to be examined in the region of the pupil thereof. Thereafter, the user can observe the interior of the eye to be examined by looking more or less perpendicularly onto the plane surface 5 or through the contact glass 1.

Of course, the contact glass 1 can also be used to treat the eye, for example for laser applications.

FIG. 3 shows a sectional view through another variant of a contact glass, the design of the contact surface 6.3 of the base body 2.1 being convex, that is to say cambered inward. Accordingly, the contact surface 6.4 of the attachment body 3.1 is of concave design, that is to say cambered outward. The cambers of the two contact surfaces 6.3, 6.4 need not be exactly the same, but they do correspond approximately.

The attachment body 3.1 is of funnel-shaped design. It has a side wall 8 that runs around and covers the base body up to approximately half of it. As a result, when the contact glass 1.1 is placed on an eye, the base body 2.1 touches neither the eye itself, nor an eyelid, the eyelashes or any other part of the patient.

A possible variant of how the base body 2.2 can be disconnectively connected to the attachment body 3.2 is illustrated in FIG. 4. The attachment body 3.2, once again of funnel-shaped design, has at the upper edge of the funnel on the inside a comb-type protuberance 9 that runs round completely or partially and latches into a corresponding annular groove 10 on the base body 2.2 upon combination with the base body 2.2. The annular groove 10 can either likewise run round the base body 2.2 completely, or it can also be interrupted in order, for example, to prevent the mutual rotation of base body and attachment body.

FIGS. 5, 6 and 7 show a further contact glass 1.3. FIG. 5 shows a sectional view of the non-combined contact glass 1.3, FIG. 6 a sectional view of the combined contact glass 1.3, and FIG. 7 a further sectional view of the combined contact glass 1.3 along a plane of section 11.1 situated perpendicular to the rotation axis 4.

In order to ensure an interspace 12 between the base body 2.3 and the attachment body 3.3, once again of funnel-shaped design, of the combined contact glass 1.3, a plurality of elongated webs 13.1, 13.2, 13.3 running from top to bottom are provided on the inside of the attachment body 3.3. Since longitudinal sections along the plane of section 11.2 are involved in FIGS. 5 and 6, only one web 13.1 is visible in each case. Its dimensions are selected in such a way that with the contact glass 1.3 combined a specific spacing is achieved between the two contact surfaces 6.3, 6.4 of the base body 2.3 and the attachment body 3.3

The interspace 12 could, of course, also be achieved by applying such webs or other protuberances to the outside of the base body 2.3. Alternatively, the inside of the attachment body 3.3 or the outside of the base body 2.3 would be provided with corresponding grooves. However, this would have the disadvantage that it would be contaminated more quickly.

FIGS. 5 and 6 show yet a further aspect. Before the combination of base body 2.3 and attachment body 3.3 to form the contact glass 1.3, it is firstly possible to apply a specific quantity of an optically transparent, deformable, for example gel-type liquid 14 to the contact surface 6.4. Upon combination of the contact glass 1.3, the liquid 14 is compressed between base body 2.3 and attachment body 3.3 and distributed uniformly between the two contact surfaces 6.3, 6.4.

If too much liquid 14 is applied, the excess liquid 14 can escape into the interspace 12. However, not only excess liquid 14, but also the air located between the two contact surfaces 6.3, 6.4 can escape into the interspace 12.

There is thus no longer any air between the base body 2.3 and the attachment body 3.3. If the gel-type liquid 14 is now selected in such a way that its refractive index corresponds approximately to the refractive index of the base body 2.3 or attachment body 3.3, the reflection of optical beams at the interfaces between the various materials can, as already mentioned, be reduced. In other words: the contact surfaces need not have a high optical surface quality. In particular, an expensive antireflection coating susceptible to damage can be eliminated. Of course, the materials used for the base body 2.3 and attachment body 3.3 are also selected in such a way that, on the one hand, their refractive index is equal or at least virtually equal, and this refractive index is approximately equal to the refractive index of the eye.

In the case of a refractive index of the eye of approximately 1.33, and of a contact glass with refractive index 1.5, a residual reflection of approximately 4 per thousand is reached, residual reflections of up to approximately 5 per thousand constituting no problem. The gel-type liquid 14 is selected correspondingly with a refractive index in the region of approximately 1.3 to 1.7.

A large selection of liquids that can be used for this index matching is available. A liquid known in eye treatment is, for example, a two-percent solution of methylhydroxypropylcellulosum with sodium chloride and benzalconium chloride as preserving agent, known under the name of Methocel 2%.

Instead of using a liquid 14 for the index matching, it is also possible to use other materials, for example so-called solid gels. As an example, mention may be made of a transparent silicone film of elastically deformable thickness that is introduced between the two contact surfaces before the combination of the contact glass. In order there, as well, to avoid the inclusion of air between the contact surfaces, the film at the center can be raised, for example, or the cambers of the contact surfaces can be appropriately designed.

FIG. 8 shows a contact glass from FIG. 6 as it is placed on an eye 15. Also illustrated are the two eyelids 16 with the eyelashes 17.

The raised side wall 8 of the attachment body 3.3 prevents the eye 15, the eyelids 16 or the eyelashes 17 coming into contact with the base body 2.3. That is to say, the base body 2.3 need not be sterilized after each use, it suffices to disinfect. Furthermore, the attachment body 3.3 can be designed in such a way that it can be sterilized. By contrast, it is less complicated and correspondingly cost effective— since the attachment body 3.3 can be produced in a simple way, for example by means of injection molding, from inexpensive materials—to design the attachment body 3.3 as a disposable item that is discarded after being used once or after a few uses. A multiplicity of known methods and means are likewise available for the disinfection or sterilization.

Figure 9:
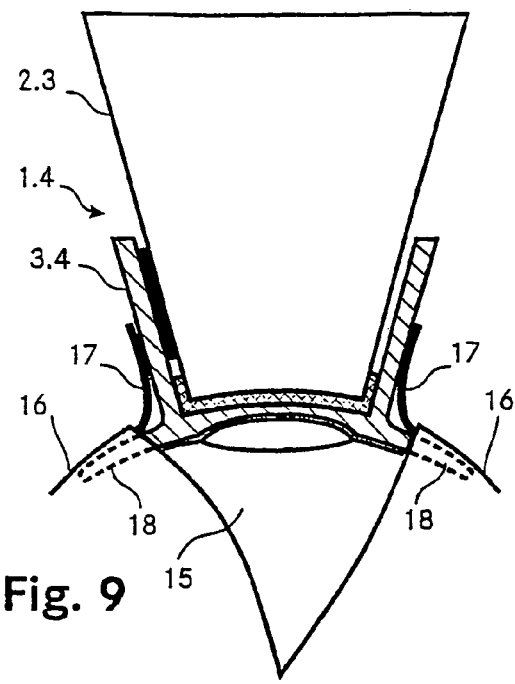
FIG. 9 shows a contact glass, placed on an eye, with an attachment body having a scleral ring.

FIG. 9 illustrates, once again, the eye 15 with eyelids 16 and eyelashes 17, together with a contact glass 1.4 placed on. The latter has the same base body 2.3 as the contact glass 1.3 from FIG. 8, but another attachment body 3.4.

The attachment body 3.4 is fitted with a so-called scleral ring 18. As illustrated, when the attachment body 3.4 is placed on the eye 15 said scleral ring is pushed under the eyelids 16 and held firmly in its position by the latter. The scleral ring can either run entirely round the attachment body, or it is present only in specific regions, for example in the region of the eyelids 16.

Figure 10:
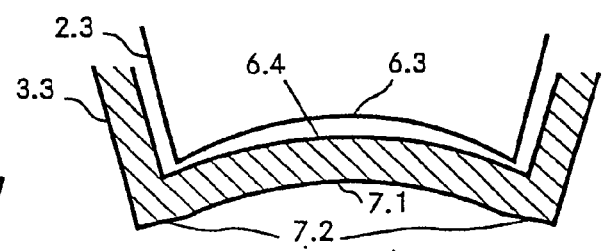
FIG. 10 shows a section, illustrated in an enlarged fashion, of the contact glass from FIG. 8.

FIG. 10 illustrates an enlarged section of the contact glass 1.3 from FIG. 8, the gel-type liquid 14 having been omitted for greater clarity. It shows the different cambers of the various boundary surfaces of the contact glass 1.3. The contact surface 6.3 of the base body 2.3 has, for example, a smaller radius of curvature than the contact surface 6.4. It is further to be seen that the touch surface 7 of the attachment body 3.3 has two differently curved regions 7.1 and 7.2 for the purpose of resting optimally on an eye. The central regions 7.1 with the smaller radius of curvature, which corresponds approximately to the radius of curvature of the contact surface 6.4, is conceived for positioning over the region of the pupil of the eye, which is somewhat raised as a rule. The outer regions 7.2 with a larger radius of curvature comes correspondingly to be situated on the less strongly curved regions around the pupil.

However, it is to be stressed that many other arrangements with other radii of curvature or with centers of curvature selected otherwise are also possible. Thus, for example, the radius of curvature of the contact surface 6.3 can be greater than that of the contact surface 6.4. Furthermore, one or both contact surfaces 6.3, 6.4 could also be of flat design, or have a curvature in the opposite direction.

Figure 11:
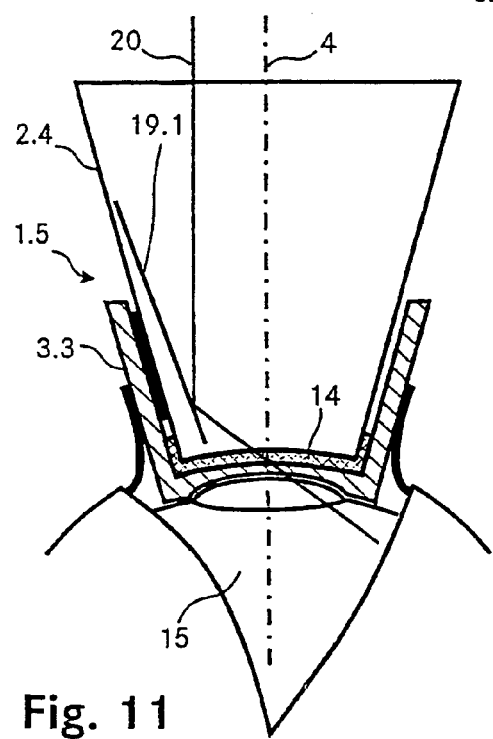
FIG. 11 shows a contact glass, placed on an eye, with a base body having a mirror.
Figure 12:
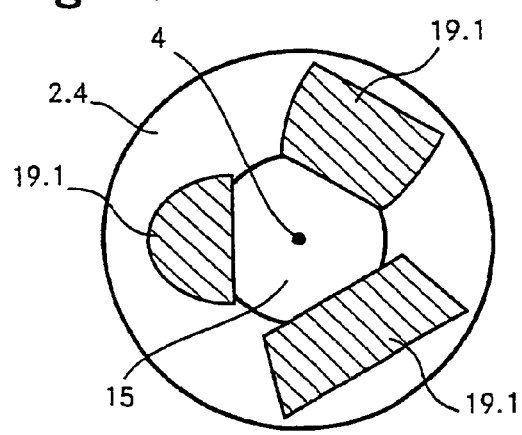
FIG. 12 shows the contact glass from FIG. 11, seen from above.

FIGS. 11 and 12 show a contact glass 1.5 placed on the eye 15, with the attachment body from FIG. 8. The base body 2.4 illustrated here has, however, a multiplicity of mirrors 19.1, 19.2, 19.3 positioned laterally in the base body 2.4, only the mirror 19.1 being visible in the sectional illustration in FIG. 11. The mirrors 19.1, 19.2, 19.3 are each designed for examining different lateral regions of the interior of the eye 15 and are correspondingly differently shaped or have different angles of inclination to the rotation axis 4. The mirrors 19.1, 19.2, 19.3 are produced, for example, by grinding the base body 2.4 plane in the desired region with the corresponding angle of inclination, the incidence of extraneous light being prevented with the aid of a sleeve (not illustrated) of the base body 2.4.

FIG. 11 further illustrates a light beam 20 that enters the contact glass 1.5 parallel to the rotation axis 4 and is deflected at the mirror 19.1 such that it is directed through the gel-type liquid 14 and the attachment body 3.3 into a lateral region of the eye 15. Such a light beam 20 penetrating into the eye 15 is used, for example, to illuminate the interior of the eye 15. If, however, the light beam 20 runs in the direction illustrated out of the eye through the contact glass, it can be observed by the user.

Not considered in the course of the light beam 20 is the refraction at the various boundary surfaces of the eye 15 and the contact glass 1.5, respectively, therebetween. To be precise, depending on the geometry selected for the constituents of the contact glass 1.5, it is also possible to achieve various optical effects such as a specific magnification, or else different fields of view inside the eye 15.

In order to examine completely the lateral inner region, observable with the aid of the mirror 19.1, of the eye 15, the base body 2.4 need only be rotated about its rotation axis 4. The attachment body 3.3 remains placed on the eye 15 without itself being moved, and can therefore also not cause any injury on the eye 15. The liquid 14 facilitates this rotation of the base body 2.4 in the attachment body 3.3.

It may be stated in summary that the invention permits a multiplicity of devices for examining and/or treating eyes to be combined with the aid of a few base bodies and a few types of attachment bodies, instead of using a device specifically provided for the purpose of each examination/treatment. In addition, because it does not come into contact with the eye during examination and/or treatment, the base body can be made from a material that need not be sterilizable, and is correspondingly less expensive and easier to process.

The invention claimed is:

1. A device for examining and/or treating an eye, comprising:
   a base body; and
   an attachment body combinable with the base body, the base body having a first contact surface and the attachment body having a second contact surface and a touch surface, the device being configured to be placed on the eye with the touch surface of the attachment body, wherein
   the touch surface is positioned opposite the second contact surface,
   the second contact surface has substantially the same shape as the first contact surface, and
   the attachment body is combinable with the base body so that the contact surfaces are situated substantially parallel to one another.

2. The device as claimed in claim 1, wherein the base body and the attachment body can be rotated relative to one another.

3. The device as claimed in claim 2, wherein the base body and the attachment body can be rotated relative to one another about an optical axis.

4. The device as claimed in claim 1, wherein at least one of the base body and the attachment body has at least one distancing element for maintaining a minimum spacing between the base body and the attachment body, the at least one distancing element is positioned outside at least one of the first surface and the second contact surface.

5. The device as claimed in claim 4, wherein at least one of the base body and the attachment body has a plurality of protuberances for maintaining the minimum spacing between the base body and the attachment body.

6. The device as claimed in claim 4, wherein the device has an optically transparent, deformable intermediate material between the first and second contact surfaces.

7. The device as claimed in one of claims 1 to 4, wherein when the device is placed on the eye of a patient, only the attachment body is in contact with the patient.

8. The device as claimed in claim 7, wherein the attachment body is held on the base body via one of a positive connection that can be disconnected and a non-positive connection that can be disconnected.

9. The device as claimed in claim 1, wherein the base body is configured to enable an ophthalmological examination andlor treatment of the eye.

10. The device as claimed in claim 9, further comprising:
a mirror for examining and/or treating one of a lateral inner region and a chamber angle of the eye.

11. The device as claimed in claim 1, wherein
the attachment body has a contact surface substantially adapted to a surface region of the eye to enable the attachment body to be placed on the eye.

12. The device as claimed in claim 11, wherein the contact surface has edge regions which can be pushed under at least one eyelid of the patient.

13. The device as claimed in claim 11, further comprising:
a plurality of attachment bodies combinable with the base body, wherein each attachment body is individually packaged and housed in a container ready for use.

14. The device as claimed in claim 11, where the attachment body can be disinfected or sterilized.

15. The device as claimed in claim 13, wherein the attachment body is packed in a sterile fashion, and is housed in the container so that an attachment body is combinable with the base body without holding contact of the attachment body and with an optically transparent, deformable, intermediate material introduced between the base body and the attachment body.

* * * * *